United States Patent
Erskine-Smith

(10) Patent No.: US 9,572,635 B2
(45) Date of Patent: Feb. 21, 2017

(54) DENTAL WEDGE

(71) Applicant: Erskine Products Pty Ltd, North Curl Curl (AU)

(72) Inventor: Craig Mathew Erskine-Smith, North Curl Curl (AU)

(73) Assignee: Erksine Products Pty Ltd, North Curl Curl (AU)

( * ) Notice: Subject to any disclaimer, the term of this patent is extended or adjusted under 35 U.S.C. 154(b) by 59 days.

(21) Appl. No.: 14/371,939

(22) PCT Filed: Jan. 9, 2013

(86) PCT No.: PCT/AU2013/000012
§ 371 (c)(1),
(2) Date: Jul. 11, 2014

(87) PCT Pub. No.: WO2013/104017
PCT Pub. Date: Jul. 18, 2013

(65) Prior Publication Data
US 2014/0356811 A1    Dec. 4, 2014

(30) Foreign Application Priority Data

Jan. 13, 2012   (AU) .................................. 2012900139

(51) Int. Cl.
*A61C 5/12* (2006.01)
*A61C 3/10* (2006.01)
(52) U.S. Cl.
CPC ................ *A61C 5/127* (2013.01); *A61C 3/10* (2013.01)

(58) Field of Classification Search
CPC ......... A61C 5/127; A61C 5/125; A61C 15/00; A61C 15/02; A61C 3/10
(Continued)

(56) References Cited

U.S. PATENT DOCUMENTS

| 2,867,905 A | 1/1959 | Meacham |
| 3,590,814 A | 7/1971 | Bennett et al. |

(Continued)

FOREIGN PATENT DOCUMENTS

| EP | 0 668 060 A2 | 8/1995 |
| EP | 0668060 A2 | 8/1995 |
| EP | 1815819 A1 | 8/2007 |

OTHER PUBLICATIONS

Partial Supplementary European Search Report mailed Nov. 4, 2015 in EP Patent Application No. 13735997.2, 6 pages.
(Continued)

*Primary Examiner* — Nicholas Lucchesi
(74) *Attorney, Agent, or Firm* — Kilpatrick Townsend & Stockton LLP

(57) ABSTRACT

A dental wedge (10) having a wedge body (11) and a gripping portion (12). The wedge (10) also has a longitudinal axis (13). The body (11) extends from a first end (14) to a second end (15), with the gripping portion (12) attached to the first end (15). The body (11) is constructed of at least two longitudinally extending layers. In one embodiment there are three layers, a first longitudinally extending layer (16), and second longitudinally extending layer (17) and a third longitudinally extending layer (18). The layer (17) is located between the layers (16, 18). In one embodiment the layers (16, 18) are formed of a softer material than the layer (17). In an alternative embodiment the layers (16, 18) are formed of a harder material than the material forming the layer (17).

7 Claims, 14 Drawing Sheets

(58) Field of Classification Search
USPC .............................. 433/39, 40, 72, 148, 149
See application file for complete search history.

(56) References Cited

U.S. PATENT DOCUMENTS

| | | | | |
|---|---|---|---|---|
| 6,375,463 B1* | 4/2002 | McLean | ................. | A61C 5/127 |
| | | | | 433/149 |
| 6,402,514 B1* | 6/2002 | Fischer | ................. | A61C 5/127 |
| | | | | 433/149 |
| 6,439,886 B1* | 8/2002 | Thoreson | ............... | A61C 5/125 |
| | | | | 433/155 |
| 6,468,080 B1 | 10/2002 | Fischer et al. | | |
| 8,177,553 B2* | 5/2012 | Stoll | ...................... | A61C 5/125 |
| | | | | 132/329 |
| 2002/0055084 A1* | 5/2002 | Fischer | ................. | A61C 5/125 |
| | | | | 433/149 |
| 2004/0014006 A1 | 1/2004 | Garrison et al. | | |
| 2006/0243409 A1* | 11/2006 | Fish | ...................... | A61C 15/02 |
| | | | | 162/329 |
| 2007/0148613 A1* | 6/2007 | Stoll | ...................... | A61C 5/125 |
| | | | | 433/39 |
| 2008/0064000 A1* | 3/2008 | Clark | .................... | A61C 5/125 |
| | | | | 433/29 |

OTHER PUBLICATIONS

International Search Report and Written Opinion mailed Apr. 17, 2013, from PCT Application No. PCT/AU2013/000012 (6 pages).
Australian Examiner's Report of Aug. 31, 2016 of related Australian application (three pages).

* cited by examiner

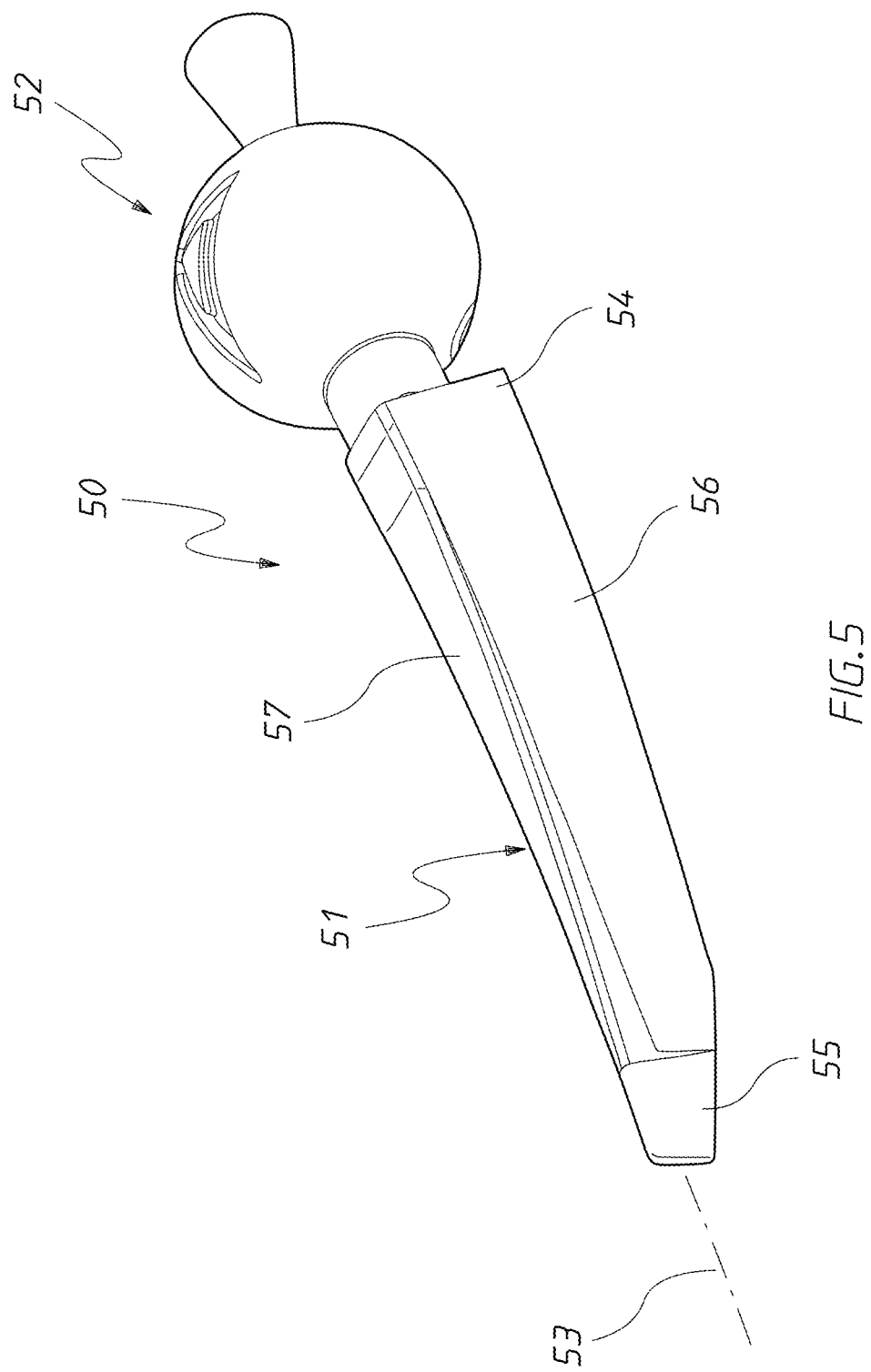

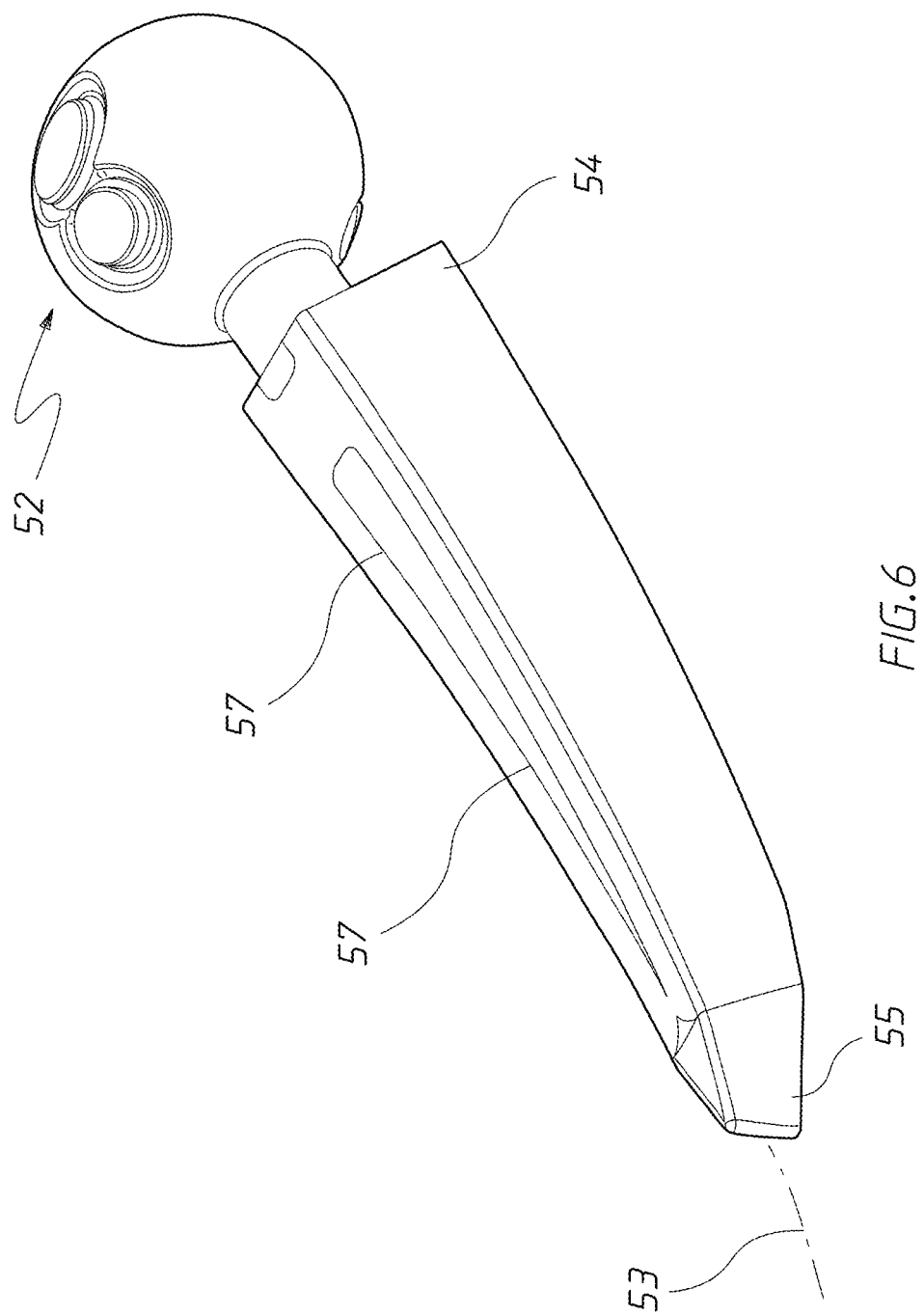

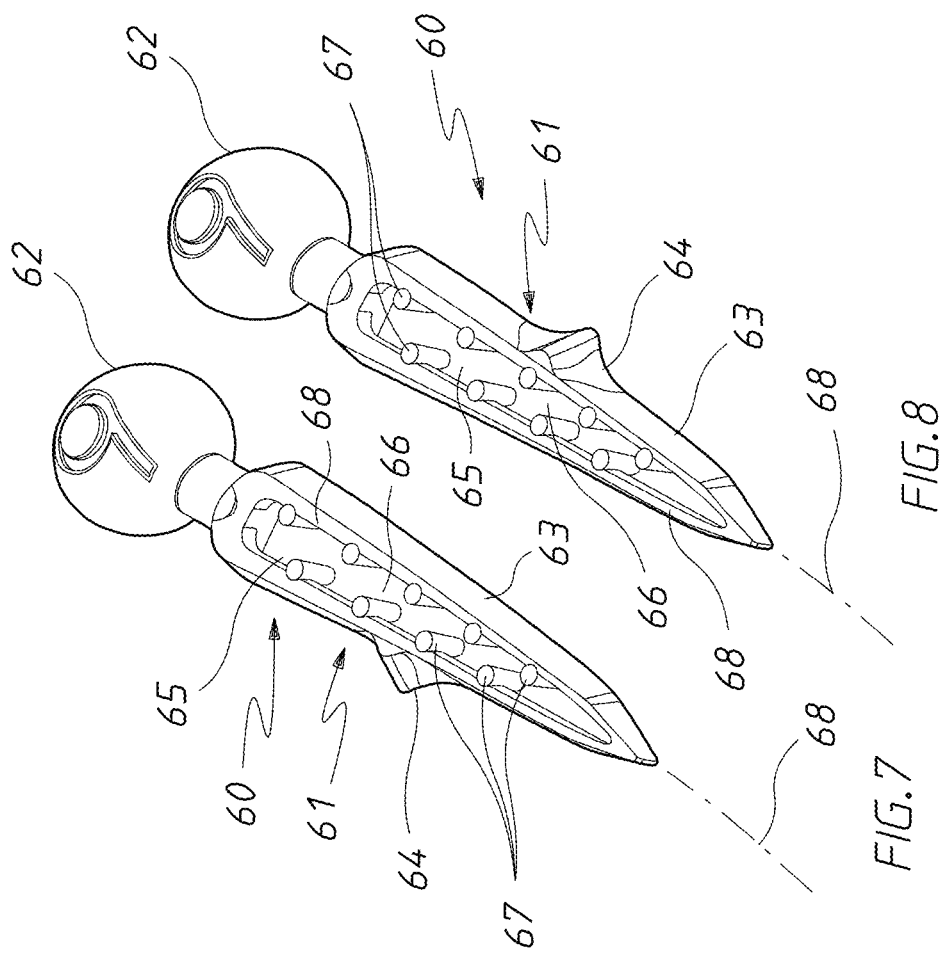

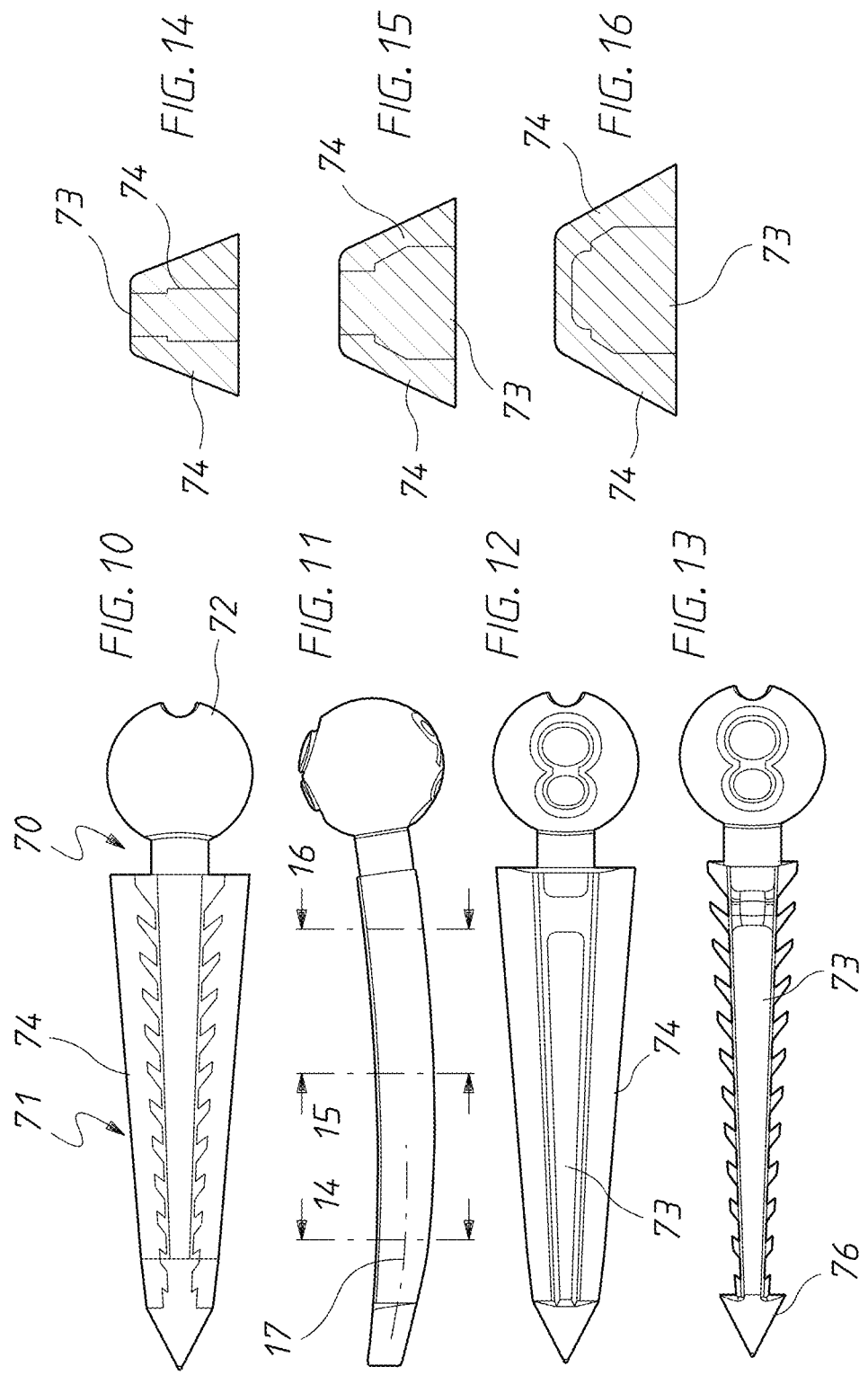

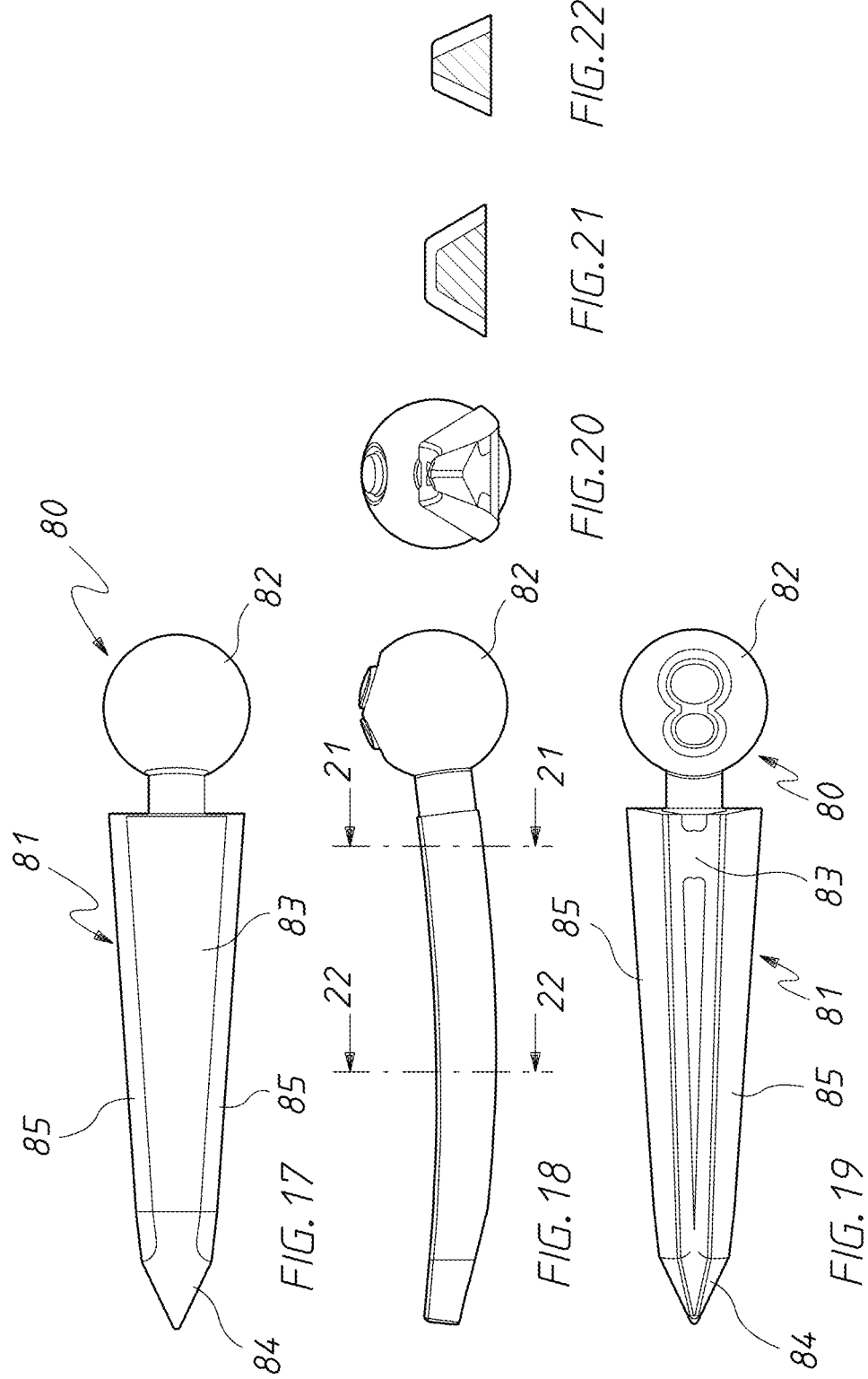

DENTAL WEDGE

CROSS-REFERENCE TO RELATED APPLICATION

This application is a U.S. National Phase of International Application No. PCT/AU2013/000012, filed Jan. 9, 2013, which claims priority from Australian Application No. 2012900139, filed Jan. 13, 2012, the disclosures of which are incorporated by reference herein.

FIELD

The present invention relates to dental wedges and more particularly but not exclusively to dental wedges that aid in retaining in place bands employed in dental restoration.

BACKGROUND

Traditionally, dental wedges have been primarily used to reduce the incidence of excessive restorative material being pushed between the restoration "formwork" (or the "matrix band" as it is known in dental parlance) and the edge of the tooth in the region of the gum in between the teeth. Such protrusions . . . "overhangs" as they are known, cause floss to snag, and/or fray, cause bacteria and food and plaque to accumulate under the ledge, and can lead to periodontal disease and bone loss, plus increase the chances of future decay. Wedges also serve the dual purpose of stabilising the matrix band. This is especially important when a sectional matrix style of band is used as opposed to the circular toffelmire, sequland or auto matrix type band, which get a grip on the tooth by virtue of their 360° locking on, clamping action, as opposed to the limited 45 degree slice of the tooth the sectional matrix band typically sits next to.

Wedges were nearly always made of timber or wood (often sycamore) but in recent decades there has been a trend to make them from polymer materials, with varying degrees of success. Wedges were always made from flexible, moldable materials in order to adapt to the variable contours and space sizes between the teeth, but were never generally designed to provide substantial springback force when compressed, rather they were usually only able to flex to adapt, not to push back. As a result, virtually all wedges on the market need to be either used with additional equipment, or tightened on multiple occasions.

Wedges made of wood have the disadvantage that they have very little resilience or spring back power because they need to be stiff enough to push into the gap between the teeth at high force without buckling. Although they worked quite well to adapt to the curvature of the teeth, [except in furcations] and they hold the matrix band tightly against the proximal surfaces of that portion of the tooth apical to the edge of the cavity, because of their lack of resilience, they often resulted in poor quality tooth separation and thus poor quality contact points when the matrix band was removed. This is because removal of the matrix band creates a gap equal to the thickness of the band, and it is necessary to separate the teeth within their semi flexible and visco elastic tissue matrix during the course of the restorative procedure before the filling is hardened, at least by the thickness of the matrix band, so that the teeth touch firmly with no inter proximal gap once the band is removed.

This was not a problem in the past but now is due to the increasing use of composite resin. Composite resin restorations differ from other restorations like amalgams in that the lateral force applied by the restorative material during the condensation and packing of the filling phase is far less. As a result of this there is less lateral pressure put on the matrix band [like formwork] and far less separation created between the adjacent teeth, such that when the matrix band is removed composite restorations typically have the above mentioned gap, which typically is just wide enough to allow meat fibres and fine fibres from vegetables such a celery to enter the gap, especially during the high forces of mastication. Such food fibres, especially meat, often contain rubbery elastin, and when forced in under active biting pressure they effectively jam an elastomeric fibre in the gap under pressure, which in turn applies a slight expansive orthodontic like force to the gap. The adjacent teeth are thus pushed apart even further in the subsequent hours and days . . . thus causing the gap to become wider. Hence a viscous circle develops and the gap enlarges to receive even more food, usually up to about a self limiting but highly irritating/damaging width of about 0.8 mm-0.5 mm, and the patient not only gets an immediate uncomfortable, very annoying and irritating problem, but probably gum disease and decay in subsequent years from the impacted food.

As more of the world's dentists turn away from unsightly and mercury containing metallic amalgam, and use composite resin based restoratives for their primary restorative material, so this problem will increase, especially in third world countries where contact pressure may be seen as an optional peripheral refinement, not commercially justified given the lower fee level and time allowed, and a minor issue compared to the main concern of getting decay out and a filling of any kind into the hole. Even in sophisticated western markets it has been reported that as many as 60% of fillings done in composite [white] material result in food traps. [CRA survey] In the period prior to 1990 when the predominant restorative material throughout the world was metal amalgam, this was not such a large problem because amalgam condensation created such high lateral packing pressure it separated the teeth sufficiently so that on removal of the matrix the contact point was sufficiently tight so as not to routinely cause this food impaction problem.

Food packing between teeth however will soon manifest its serious side to those dentists new to composite, who wrongly assume that composite is the same as amalgam in outcome. Food trapping can cause devastating consequences for the patient with time. The bone loss caused by such food packing is usually irreversible and any decay caused by such food packing is usually at a point deep down next to the gum and often well below the gum at the bone level, where it is harder to restore, and where the tooth surface tapers in close to the pulp, or nerve. The nerve is much closer to the encroaching decay than with the usual interproximal and occlusal decay. This fact, combined with the generous nutrient supply from the trapped food to the bacteria making the decay, can cause the decay to start and advance quickly to the nerve, and for it to be infected and destroyed in an alarmingly short time. A dead nerve, apart from being painful, requires expensive root canal therapy, then a crown, but the margins of such crown have to be placed in a compromised sub gingival position right in the most difficult area for the patient to maintain in a plaque free state, (interproximally) and so the chances of periodontal disease and secondary caries increase around this crown. A second crown may be impossible to do because of the unrestorable nature of the sub gingival defect, leading to extraction of the tooth, and the need for an implant or denture or bridge, each with their own set of new risk factors. Thus it can be seen that a series and a lifetime of problems can potentially flow from the simple misadventure of a poorly executed composite resin restoration which results in an open or light contact point pressure with subsequent food trapping.

As a result of the inadequacy of wooden wedges to provide sufficient rebound effect and insufficient separating power, and as a result of the inadequacy of all the existing polymeric wedge wood substitutes to provide adequate separating power, a large industry has developed around the concept of providing separation between the teeth with other devices during the course of the restorative procedure. Instruments such as contact-pro have been used internally within the cavity to lever the teeth apart, and a large section of the general dental community now rely on the provision of metal rings with two legs, with trade names such as Compositite, palodent bitine rings, Garrison rings, Vrings etc to squeeze into the embrasure space between the teeth such that the vectors of force created by the squeezing ring legs apply a separating force between the teeth at the point where the restoration is likely to be placed. The use of these rings, although moderately successful in terms of outcome is somewhat unpredictable in terms of contact point pressure due to variabilities in tooth morphology, the extent of the caries and the amount and shape of the remaining tooth to engage, and the variable geometries and vectors of force that result. Also, use of the rings system is an extra step the clinician needs to take, unlike the current invention, which seeks to stabilise the matrix band, stop overhangs, and separate the teeth adequately at the same time. Also, often these rings are impossible or very difficult to use due to inadequate amounts of tooth structure to support their position on either side of the filling, unlike separation obtained internally within in the filling (eg "contact pro" and other instruments) or via the current invention.

The above rings can also become unstable and 'ping' off in the mouth and go down the throat and cause an inhalation hazard or swallowing hazard. They also still require the use of wedges anyway to stop overhangs and/or to stabilise the sectional matrix band.

Prior wedges are generally made triangular in cross section and made with excessive bulk and especially excessive vertical dimensions at the apex of this triangle that in the opinion of the patent author cause the wedges to interfere with and intrude upon the correct shape desired from the filling. They become intrusive into the desirable contour lines of the filling and distort the smooth flowing form of the matrix band and compromise the operator's ability to get a broad contact point and anatomically correct emergence profile. As a result many restorations have large embrasure spaces, causing more food to become lodged between the teeth by lateral placement during eating, and also causing the contact point anatomy to be more of a point contact at the occlusal surface, which is well known in the dental profession to be less able to resist food impaction than a broad area contact point further toward the gingival margin.

Also the cross sectional shape of most dental wedges is usually triangular or square at the point where they are held by the pliers or tweezers that are used to place and align and drive them into the interproximal space. Most dental wedge holding devices have opposing flat surfaces, which do not allow stable grasping of triangular or square surfaces except at certain discrete angles, and thus limit the flexibility and ease of use. Not only do most wedges not have the ability to be easily orientated 360 degrees, but they also mostly cannot be easily be orientated in the two other planes due to the shape they are made in, and thus they are less comfortable to place, requiring compensatory wrist movement, and not as easy to align so as to be in the ideal trajectory for the interproximal space. The use of the spherical ball at the attachment point is lacking and is designed to overcome this problem.

OBJECT

It is the object of the present invention to overcome or substantially ameliorate at least one of the above disadvantages.

SUMMARY

There is disclosed herein a dental wedge having a longitudinal axis extending between first and second ends of the wedge, the wedge including:

a pair of longitudinally extending side surfaces that converge towards the first end;

a first longitudinally extending layer located between the side surfaces;

a second longitudinally extending layer located between the side surfaces;

a third longitudinally extending layer located between the side surfaces, with the third longitudinally extending layer being positioned so that the first layer is located between the second and third layers; and wherein the first layer is formed of a first material, the second layer is formed of a second material, and the third layer is formed of a third material with the first material having a modulus of elasticity less than the second material and the third material.

Preferably, the wedge includes a third longitudinally extending layer.

In a first preferred form, the second layer is located between the first and third layers, and the third layer is formed of a third material, the third material having a modulus of elasticity less than the second material.

Preferably, the first and third materials are the same material.

Preferably, the first layer is located between the second and third layers.

Preferably, the first material has a modulus of elasticity less than the third material.

There is further disclosed herein a dental wedge having a longitudinal axis extending between first and second ends of the wedge, the wedge including:

a longitudinally extending base tapering towards the first end; and wherein the first end is formed of the material less resilient than other portions of the base.

Preferably, the base has transversely outwardly extending projections.

Preferably, the wedge includes a gripping portion secured to the second end that aids in gripping the wedge.

Preferably, the gripping portion is a bulbous portion.

Preferably, the bulbous portion is connected to said second end by a stem.

Preferably, the gripping portion is attached to the second layer.

Preferably, the gripping portion is formed of said second material so as to be integrally formed with the second layer.

Preferably, the gripping portion is substantially spherical.

Preferably, the second layer is a base, and said first layer a covering portion of covering at least part of the base.

Preferably, said base includes a plurality of projections extending generally laterally relative to said axis.

There is further disclosed herein a dental wedge having a longitudinal axis extending between first and second ends of the wedge, the wedge including:

a longitudinally extending base extending from the first end towards the second end, with the base tapering towards the first end; and a gripping portion attached to the second end and providing surfaces extending generally transverse relative to said axis and facing toward and away from said first end.

Preferably, said gripping portion is attached to the base by a stem.

Preferably, said gripping portion is spherical.

There is further disclosed herein a dental wedge having a longitudinal axis extending between first and second ends of the wedge, the wedge including:

a longitudinally base extending from the first end towards the second end with the base tapering to the first end; and wherein the base includes at least one projection extending laterally from the base away from the axis.

Preferably, there is a plurality of projections located at intervals along the base.

Preferably, at least one of the projections is resiliently deformable relative to the base.

Preferably, at least one of the layers is a plastics polymeric material.

Preferably, at least one of the layers is a thermo plastics elastomer (TPE).

Preferably, at least one of the layers is formed of a synthetic or natural rubber.

Preferably, the wedge is longitudinally elongated.

Preferably, said axis is curved.

There is also disclosed herein, in combination any one of the above dental wedges having a gripping portion and a tool to manipulate the dental wedge, the tool including an end portion having an end extremity, said end extremity having a socket to engage the gripping portion so that a user may manipulate the tool and therefore manipulate the wedge.

Preferably, said socket includes a first socket portion and a second socket portion, the socket portions being movable relative to each other so as to be movable into clamping engagement with the gripping portion.

Preferably, the gripping portion has engagement surfaces, and each socket portion engagement surfaces, with the engagement surfaces of the gripping portion of the sockets engageable to securely attach the socket to the gripping portion when the gripping portion is clamped between the socket portions.

Preferably, said tool includes a pair of longitudinally extending arms, each terminating with a respective one of the socket portions, the arms being movable relative to each other to bring the socket portions into clamping engagement for the gripping portion.

BRIEF DESCRIPTION OF THE DRAWINGS

A preferred form of the present invention will now be described by way of example with reference to the accompanying drawings wherein:

FIG. 5 is a schematic isometric view of a modification of the dental wedge of FIG. 1;

FIG. 6 is a schematic isometric view of a further modification of the dental wedge of FIG. 1;

FIG. 7 is a schematic isometric view of a modification of the dental wedge of FIG. 1;

FIG. 8 is a schematic isometric view of a modification of the dental wedge of FIG. 7;

FIG. 10 is a series of schematic isometric views of modifications of the dental wedge of FIG. 1;

FIG. 11 is a schematic side elevation of one of the dental wedges of FIG. 10;

FIG. 12 is a schematic plan view of a further dental wedge;

FIG. 13 is a schematic side elevation of the dental wedge of FIG. 12;

FIG. 14 is a schematic further plan view of the wedge of FIG. 12;

FIG. 15 is a schematic plan view of a base of the dental wedge of FIG. 12;

FIG. 16 is a schematic end elevation of the dental wedge as illustrated in FIG. 3 sectioned along the line 16-16;

FIG. 17 is a schematic end elevation of the dental wedge of FIG. 13 sectioned along the line 17-17;

FIG. 18 is a schematic end elevation of the dental wedge of FIG. 13 sectioned along the line 18-18;

FIG. 19 is a schematic plan view of a further dental wedge;

FIG. 20 is a schematic side elevation of the dental wedge of FIG. 19;

FIG. 21 is a schematic further plan view of the dental wedge of FIG. 19;

FIG. 22 is a schematic end elevation of the dental wedge of FIG. 19;

DETAILED DESCRIPTION OF THE PREFERRED EMBODIMENT

Figure 1:
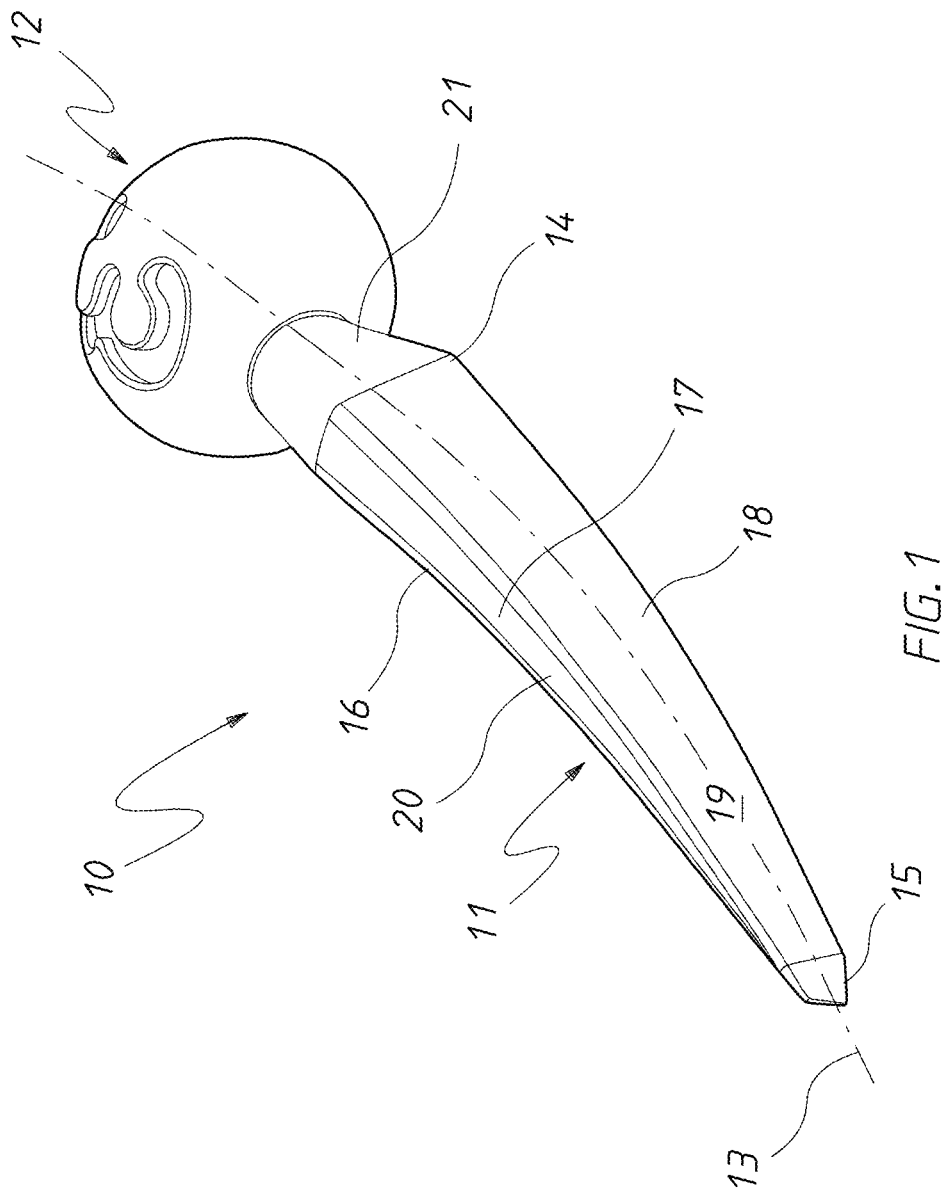
FIG. 1 is a schematic isometric view of a dental wedge.
Figure 2:
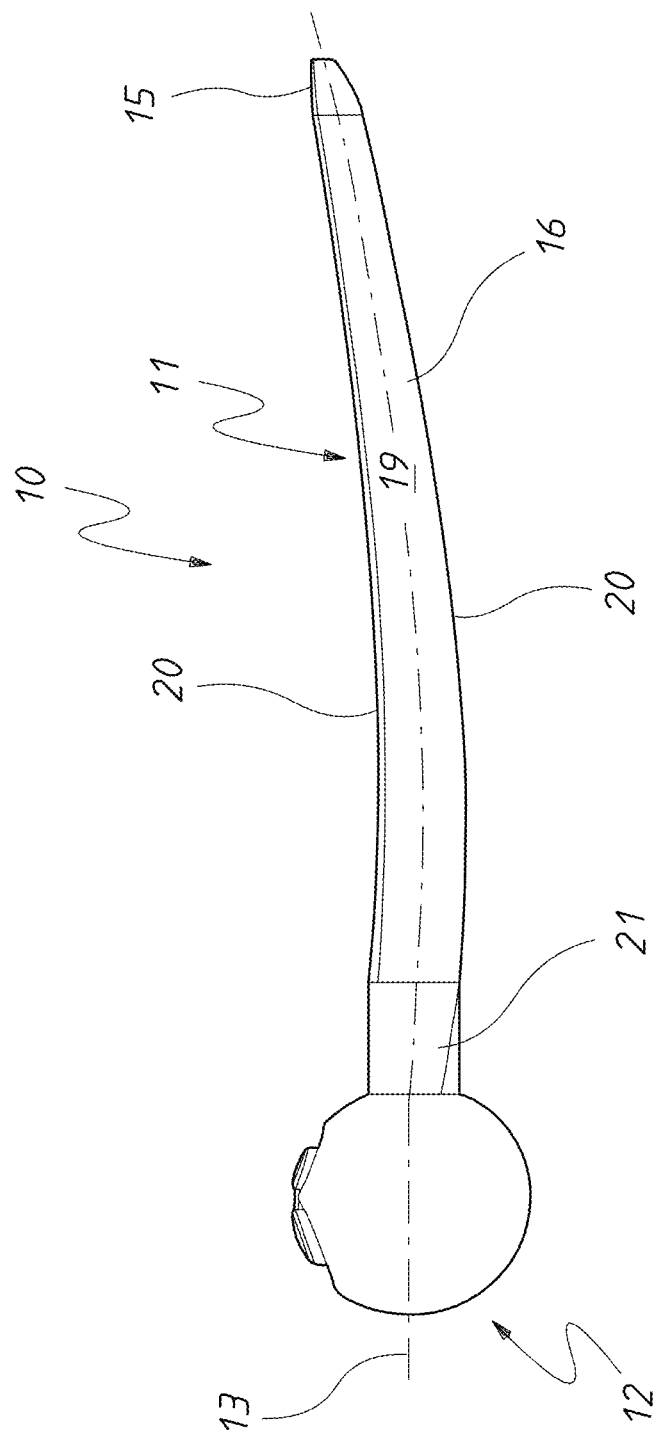
FIG. 2 is a schematic side elevation of a dental wedge of FIG. 1.

In the accompanying drawings there is schematically depicted a dental wedge 10. The wedge 10 includes a wedge body 11 and a gripping portion 12. The wedge 10 also has a longitudinal axis 13. The wedge 10 is longitudinally elongated.

The body 11 extends from a first end 14 to a second end 15, with the gripping portion 12 attached to the first end 15.

The body 11 is constructed of at least two longitudinally extending layers. In this embodiment there are three layers, a first longitudinally extending layer 16, a second longitudinally extending layer 17 and a third longitudinally extending layer 18. The layer 17 is located between the layers 16 and 18.

The body 11 has a pair of longitudinally extending side surfaces 19 that converge toward the second end 15.

The layers 16 and 18 are formed of a harder material than the material forming the layer 17. That is, the layers 16 and 18 would have a modulus of elasticity higher than the layer 17. Preferably the end portion 15 is formed of the harder material. Accordingly the end portion 15 would have a modulus of elasticity higher than the material forming the layer 17.

Preferably, materials forming the layers 16, 17 and 18 are plastics material, but may also be wood or metal in various combinations Preferably, the axis 13 is curved.

Preferably, the body 11 has longitudinally extending edge surfaces 20 that converge toward the second end 15.

Preferably, the gripping portion 12 is bulbous, and more preferably substantially spherical. Preferably, the gripping portion 12 is attached to the first end 14 by means of a stem 21.

Preferably, the body 11 is of an arcuate configuration when viewed in side elevation.

Preferably, the wedge 10 would be provided in various sizes, for example the sides 19 maybe inclined by 6°, 7° or 8°, and the thickness of the layers of 16 and 18 may be in the range of 1-2 mm with an ideal size of 1.6 mm for general use and 1.2 for deep cavities requiring low profile wedges.

The gripping portion 12 is preferably spherical so that it may be engaged by a tool manipulated by the practitioner. The tool would enable gripping of the wedge 10 at an angle that suits the practitioner who can then move the wedge angularly and rotationally as well as longitudinally.

Preferably, the gripping portion 12 would be provided with numbers or other information providing the practitioner with an indication of the size and configuration of the wedge selected.

Figure 3:
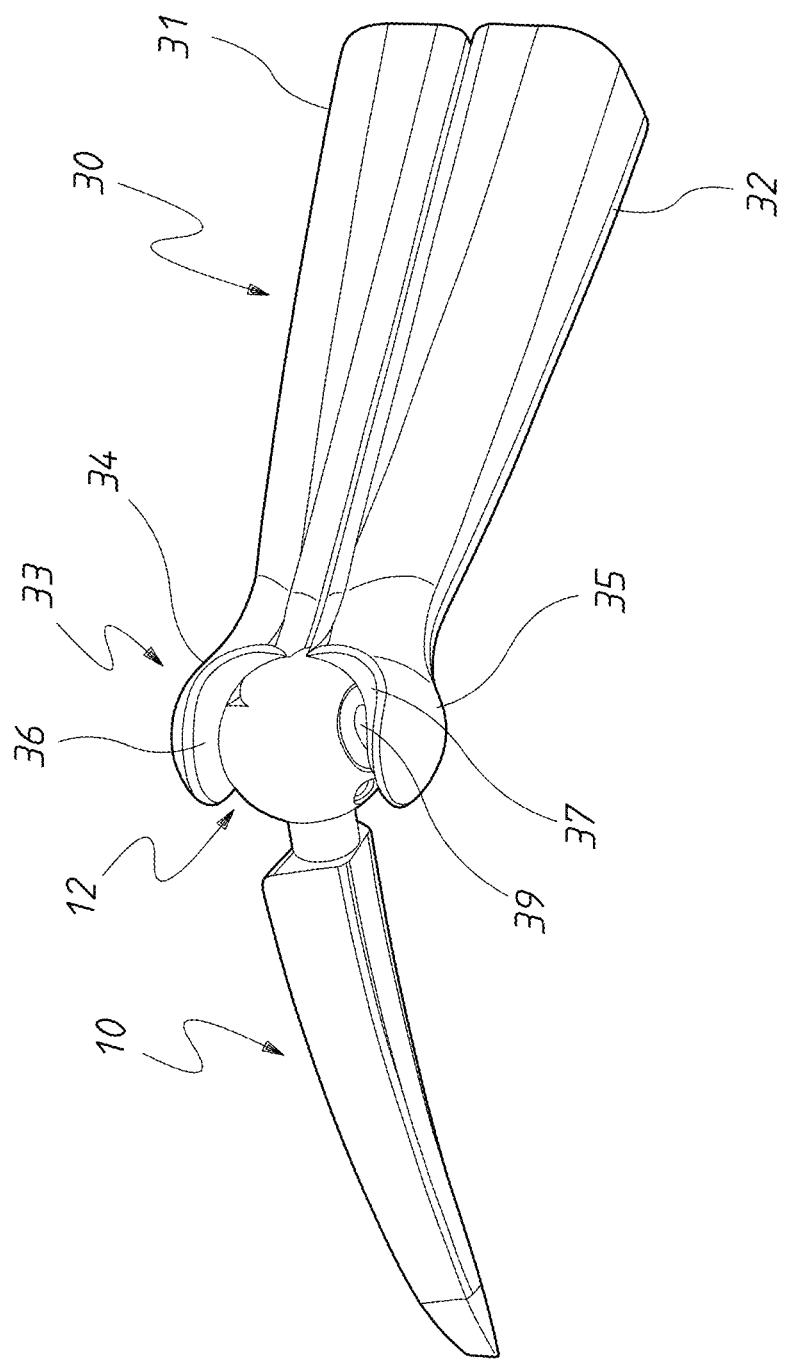
FIG. 3 is a schematic isometric view of the wedge of FIGS. 1 and 2 and a tool to engage the wedge.
Figure 4:
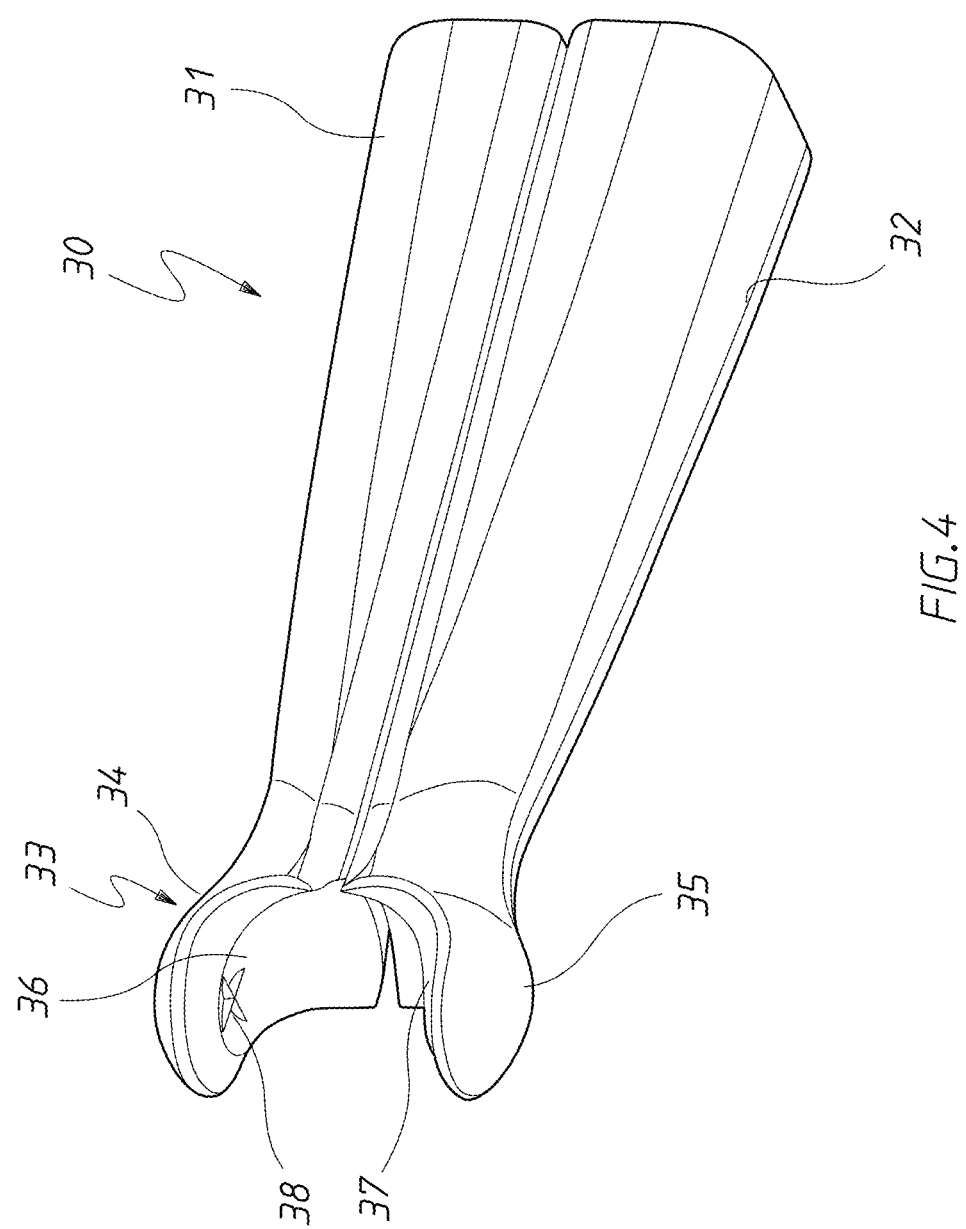
FIG. 4 is a schematic isometric view of the tool of FIG. 3.
Figure 9:
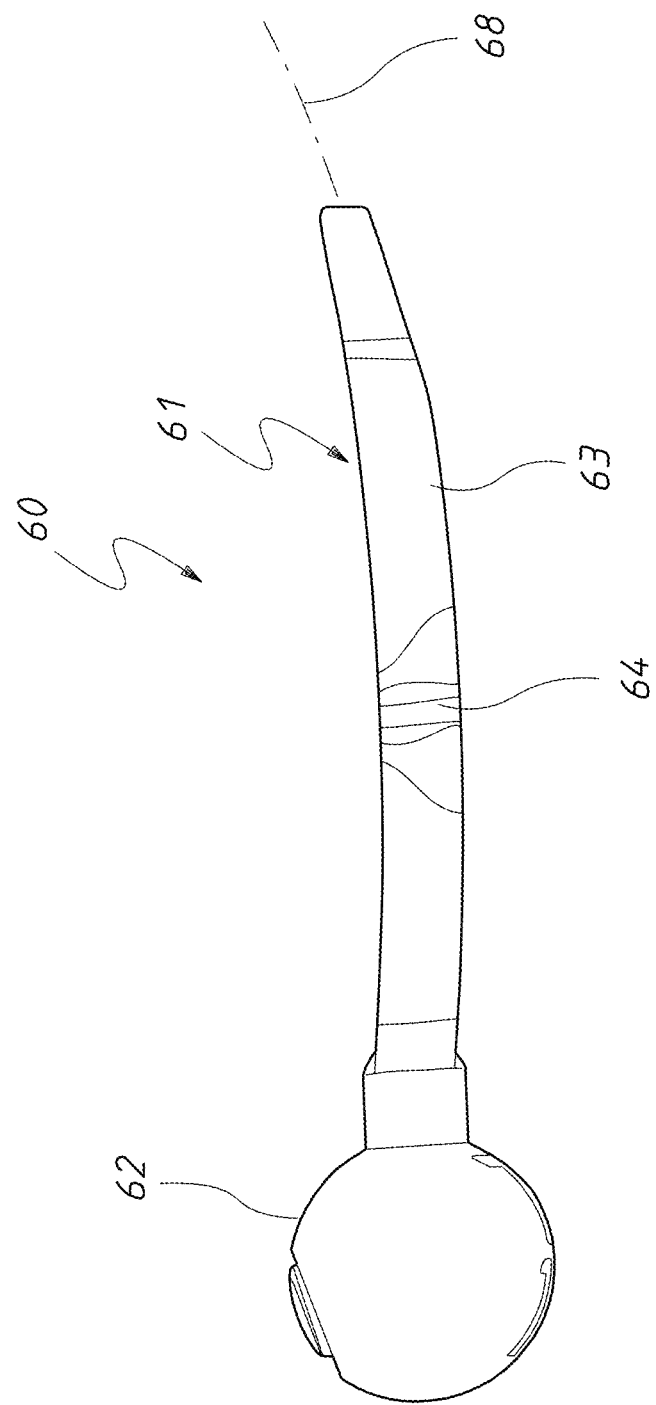
FIG. 9 is a series of side elevations and front elevations of dental wedges that are a modification of the dental wedge of FIG. 1.
Figure 23:
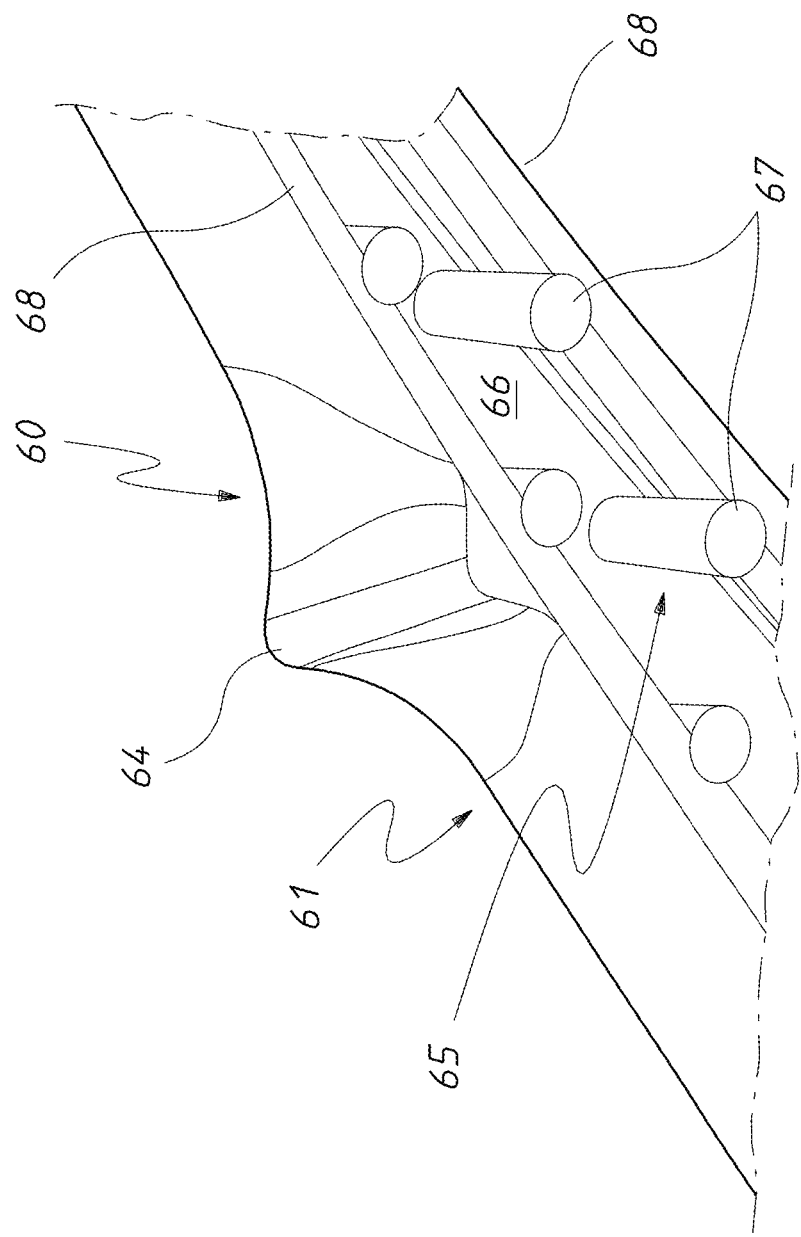
FIG. 23 is a schematic enlarged isometric view of the dental wedge of FIGS. 7 and 8.

In FIGS. 3 and 4, there is schematically depicted a tool 30 that would be engaged by a user for the purpose of gripping and manipulating the wedge 10.

The tool 30 includes a pair of generally parallel coextensive arms 31 and 32 that would be typically resiliently urged apart. The arms 31 and 32 terminate with an end portion 33 providing a socket within which the gripping portion 12 is received so as to be clamped to the tool 30 so that a user of the tool 30 may manipulate and stabilize the wedge 10, that is apply or resist axial and angular forces to the wedge 10, including applying a stabilising or active torque to the wedge 10 to cause it to enter the interproximal tooth space at the desired bucco-lingual, occluso-gingival and rotational orientation that suit the operators hand access angle, and that best relate the wedge shape and orientation to the interproximal gap shape and the desired emergence profile that is being built in the tooth restoration.

The end portion 33 includes a first socket portion 34 and a second socket portion 35 which have internal arcuate surfaces 36 and 37 that generally match the configuration of the gripping portion 12. That is the surfaces 36 and 37 would be portions of a sphere.

The surfaces 36 and 37 are each provided with a projection 38 that engages a gripping portion 12 and preferably elastically or plastically deforms the gripping portion 12 to securely connect the tool 30 and the gripping portion 12 so that the dentist may manipulate the dental wedge. Typically a user would grip the arms 31 and 32 and urge them angularly together to bring the surfaces 36 and 37 into engagement with the gripping portion 12, and the projections 38 into firm engagement with the gripping portion 12 with the tool 30 inclined to the longitudinal axis of the dental wedge at a desired angle. By releasing the arms 31 and 32, the socket portions 34 and 35 move apart to release the gripping portion 12.

In FIG. 5 there is schematically depicted a dental wedge 50. The dental wedge 50 includes a wedge body 51 and a gripping portion 52. It also has a longitudinal axis 53. The body 51 extends from an end 54 to an end 55, with the gripping portion 52 attached to the end 55. In this embodiment, the wedge body 51 includes a base 56 and a cover portion 57. The wedge 50 is longitudinally elongated.

Preferably the base 56 is formed of a harder material in the cover portion 51. Again preferably the base 56 and cover portion 57 are formed of plastics material. The base 56 provides a first layer and a cover portion 57 a second layer.

It may also be preferable to have the end 55 less resilient (harder) than the remainder of the base 56.

In the embodiment of FIG. 6, the dental wedge 50 the cover portion 57 includes a number of spaced portions 58.

In FIGS. 7 and 8, there is schematically depicted a dental wedge 60. Each dental wedge 60 includes a wedge body 61 and a gripping portion 62. The wedge 60 is longitudinally elongated.

The body 61 includes a base 63 with a lateral projection 64. The base 63 is moulded so as to provide a longitudinally extending hollow or recess having a floor surface 66. Preferably the base 63 provides a plurality of projections 67 that project into the recess 65 so that a soft material (such as natural or synthetic rubber) inserted in the recess 65 will be securely held in position by the projection 67.

In the embodiment of FIG. 7, the projection 64 extends laterally relative to the longitudinal axis 68 in one direction, while in the embodiment of FIG. 8 the projection 64 extends laterally in the opposite direction.

In FIGS. 10 to 16, there is schematically depicted a dental wedge 70. The dental wedge 70 includes a wedge body 71 and a gripping portion 72. The body 71 includes a base 73 to which there is applied a cover 74. Preferably, the base 73 is formed of a less resilient material than the cover 74. The wedge 70 has a longitudinal axis 75. The wedge 70 is longitudinally elongated.

The base 73 is integrally formed with the gripping portion 27 and terminates at an end extremity 76.

As best seen in FIGS. 14, 15 and 16, the base 73 forms a central layer, with the cover portion 74 on either side of the base 73.

In FIGS. 17 to 23, there is schematically depicted a dental wedge 80. In this embodiment, the dental wedge 80 has a wedge body 81 and a gripping portion 82. The body 81 includes a central longitudinally extending base 83 integrally formed with the gripping portion 82 and terminating at an end extremity 84. Longitudinally located on either side of the base 33 is a cover portion 85 that is formed of softer material than the base 83.

Figure 24:
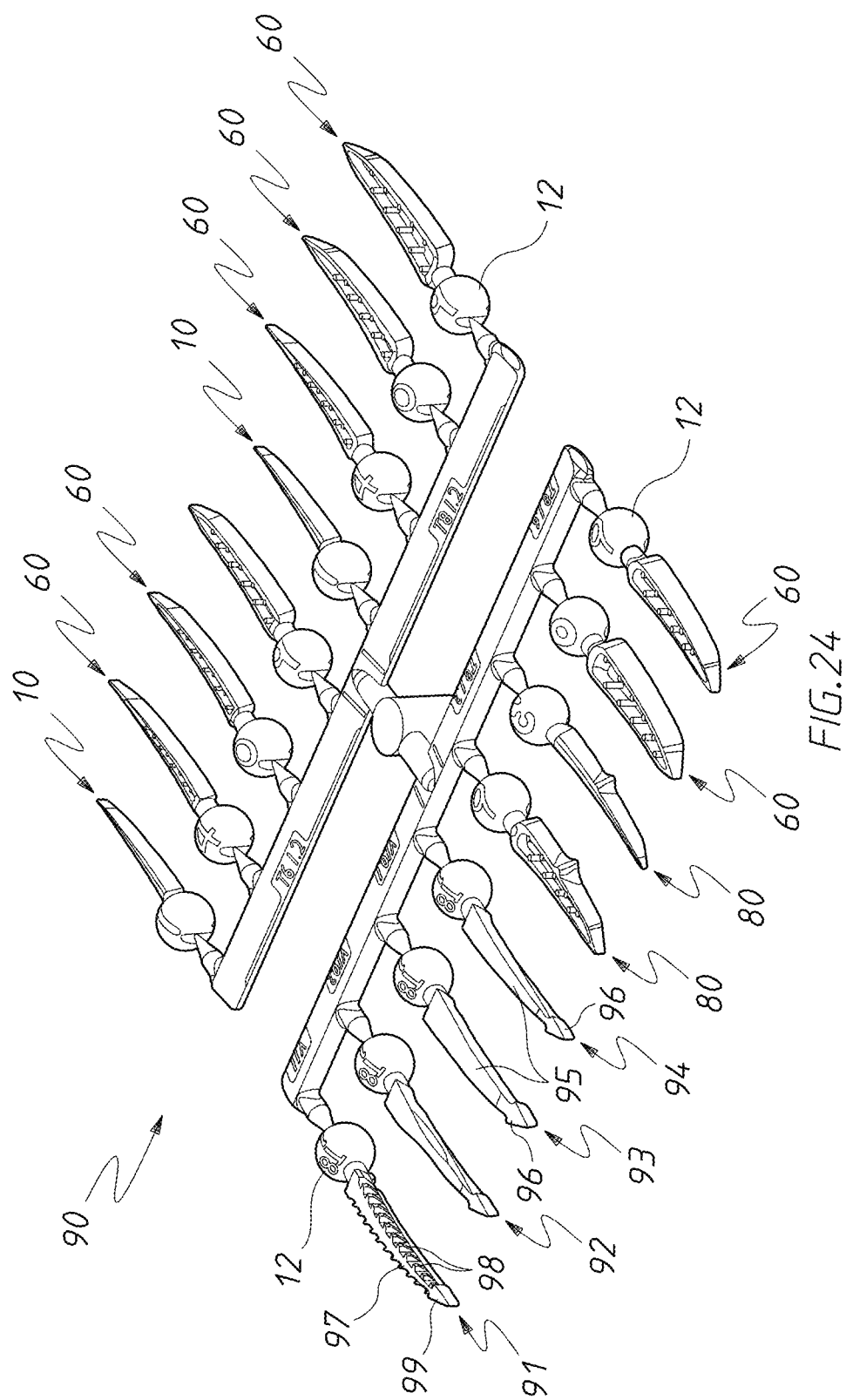
FIG. 24 is a schematic isometric view of a set of dental wedges, the set including wedges of previous Figures.
Figure 25:
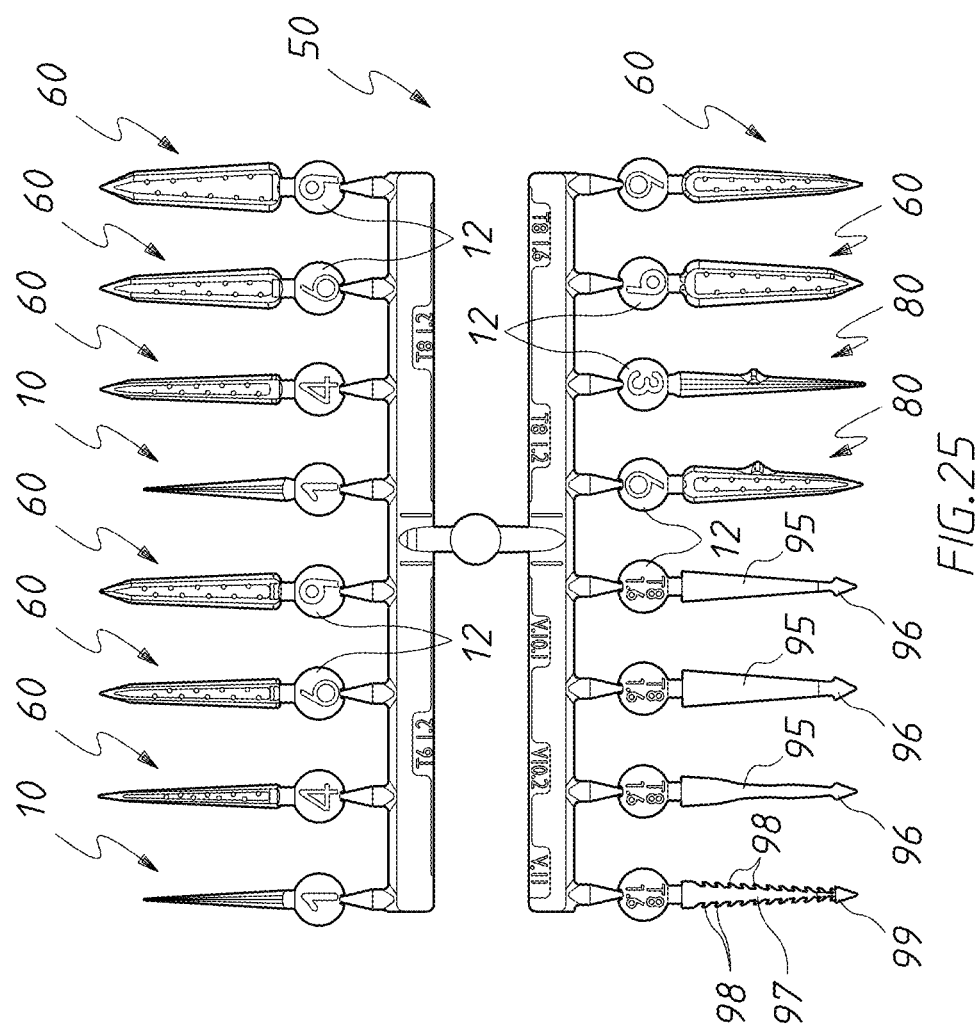
FIG. 25 is a schematic plan view of the set of wedges of FIG. 24.

In FIGS. 24 and 25 there is schematically depicted a set of wedges 90. The set 90 would be moulded as a single unit so that a dentist may select from the set 90 a desired one of the dental wedges. The set 90 includes some of the previously described dental wedges, however there are additional wedges 91, 92, 93 and 94. Each of the wedges 91 to 94 is longitudinally elongated.

The wedges 92, 93 and 94 include a longitudinally extending base 95 that tapers from the gripping portion 12 to an end portion 96.

Preferably, the end portions 96 taper to a point.

The dental wedge 91 includes a longitudinally extending base 97 with transversely outwardly projecting barbs 98 and a tapered end portion 99.

Figure 26:
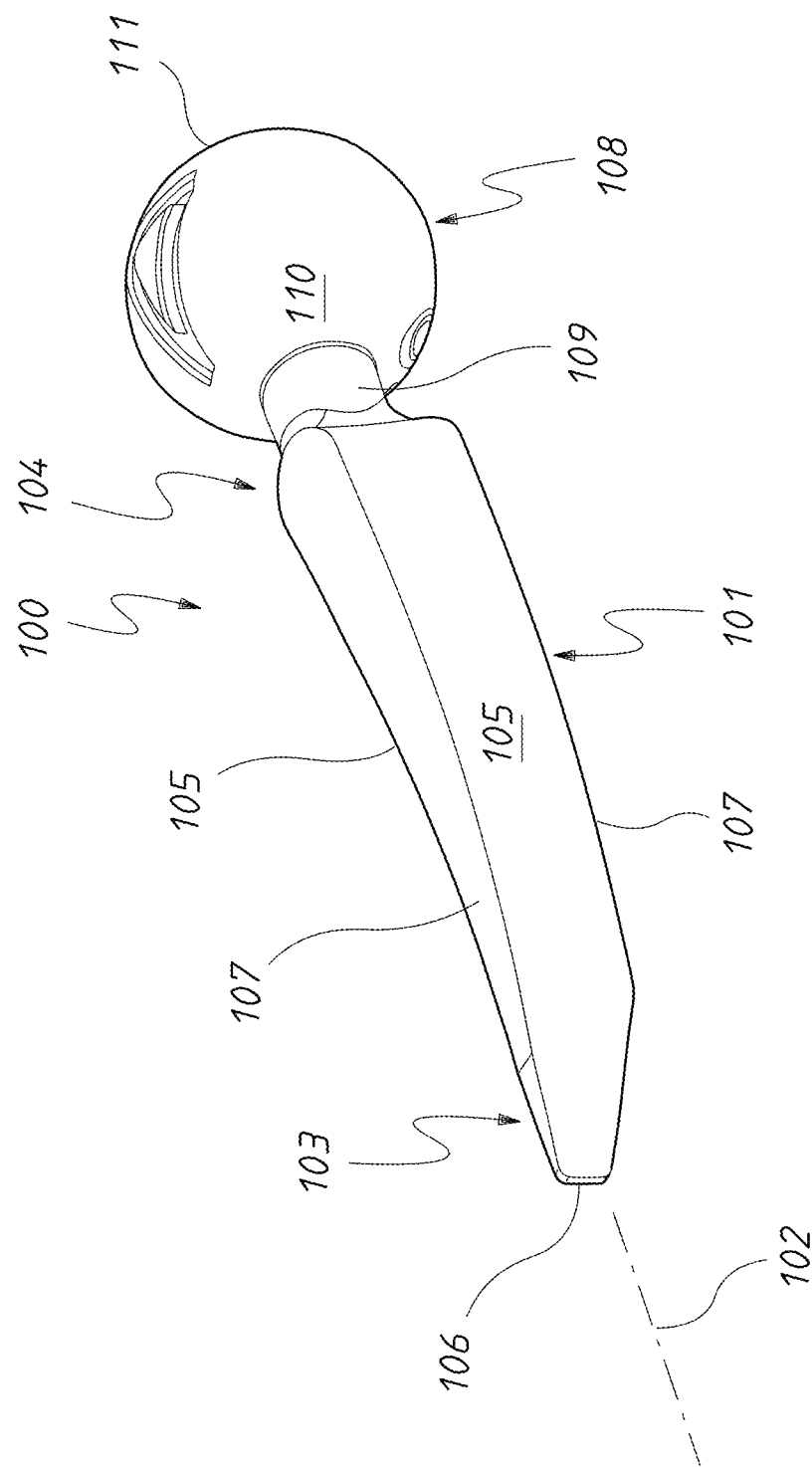
FIG. 26 is a schematic isometric view of a further dental wedge.

In FIG. 26 there is schematically depicted a further dental wedge 100. The dental wedge 100 has a base 101 having a longitudinal axis 102. The base 101 extends longitudinally relative to the axis 102 and extends from a first end 103 to a second end 104. The base 101 tapers toward the first end 103 from the second end 104 so as to be of a wedge configuration. The base 101 has longitudinally extending side surfaces 105 that converge toward the leading edge 106. Preferably, the surfaces 105 are flat and planar. The surfaces 105 are inclined by an acute angle. Preferably, the surfaces 105 are joined by longitudinally extending surfaces 107 that also converge toward the leading edge 106. The wedge 100 is longitudinally elongated.

The base 101 has secured to its second end 104 a gripping portion 108 that is preferably spherical and joined to the second end 104 by a bridge 109. The gripping portion 108 provides a surface 110 that extends generally transverse relative to the axis 102 and faces the first end 104. The gripping portion 108 also provides a surface 111 that extends generally transverse of the axis 102 and faces away from the first end 106. The surfaces 110 and 111 enable the dentist to apply a force in either direction generally parallel to the axis 102. As the gripping portion 108 is spherical, the tool 30 can engage the gripping portion 108 at a desired inclination relative to the axis 102.

The above described dental wedges may be specifically designed to be inserted into the "valley" between adjacent teeth and therefore preferably has a transverse width of between 1.2 mm and 1.6 mm. Accordingly the end portion 99 would have a modulus of elasticity considerably higher than the material forming the base 97.

The invention claimed is:

1. A dental wedge having a longitudinal axis extending between first and second ends of the wedge, the wedge including:
    a pair of longitudinally extending side surfaces that converge towards the first end;
    a first longitudinally extending layer located between the side surfaces;
    a second longitudinally extending layer located between the side surfaces; and
    a third longitudinally extending layer located between the side surfaces, with the third longitudinally extending layer being positioned so that the first layer is located between the second and third layers;
    wherein the first layer is formed of either the second material or a first material, the second layer is formed of a second material, and the third layer is formed of a third material with the first material having a modulus of elasticity less than the second material and the third material.

2. The dental wedge of claim 1, wherein the second layer and third layer are formed of the second material.

3. The dental wedge of claim 1, wherein the wedge is longitudinally elongated with said longitudinal axis being curved.

4. The wedge of claim 1, further including a gripping portion secured to the second end that aids in gripping the wedge and wherein the gripping portion is a bulbous portion.

5. The dental wedge of claim 4, wherein the gripping portion is formed of said first material and integrally formed with the first layer.

6. The dental wedge of claim 5, wherein the gripping portion is substantially spherical, and joined to the first layer by a stem.

7. The dental wedge of claim 4, wherein the gripping portion is substantially spherical.

* * * * *